US009922454B2

(12) United States Patent
Jaisson

(10) Patent No.: US 9,922,454 B2
(45) Date of Patent: Mar. 20, 2018

(54) METHOD FOR DESIGNING AN ORTHODONTIC APPLIANCE

(75) Inventor: Maxime Jaisson, Challes les Eaux (FR)

(73) Assignee: MODJAW, Ste. Helene Du Lac (FR)

( * ) Notice: Subject to any disclaimer, the term of this patent is extended or adjusted under 35 U.S.C. 154(b) by 92 days.

(21) Appl. No.: 14/241,066

(22) PCT Filed: Aug. 30, 2012

(86) PCT No.: PCT/FR2012/051957
§ 371 (c)(1),
(2), (4) Date: Jun. 6, 2014

(87) PCT Pub. No.: WO2013/030511
PCT Pub. Date: Mar. 7, 2013

(65) Prior Publication Data
US 2014/0294273 A1     Oct. 2, 2014

(30) Foreign Application Priority Data
Aug. 31, 2011 (FR) ..................................... 11 57669

(51) Int. Cl.
*G06K 9/00* (2006.01)
*G06T 17/10* (2006.01)
(Continued)

(52) U.S. Cl.
CPC ............ *G06T 17/10* (2013.01); *A61B 5/0035* (2013.01); *A61B 5/1127* (2013.01);
(Continued)

(58) Field of Classification Search
CPC ....... A61C 7/002; A61C 13/0004; A61C 7/00; A61C 9/004; G06F 17/5009;
(Continued)

(56) References Cited

U.S. PATENT DOCUMENTS 4,836,778 A * 6/1989 Baumrind ............ A61C 19/045
356/139.03
6,276,932 B1 * 8/2001 Jinnouchi ................ A61C 7/20
433/20

(Continued)

OTHER PUBLICATIONS

Furtado, Daniel Antonio, et al. "A specialized motion capture system for real-time analysis of mandibular movements using infrared cameras." Biomedical engineering online 12.1 (2013): 1.*

(Continued)

*Primary Examiner* — Jonathan S Lee
(74) *Attorney, Agent, or Firm* — Womble Bond Dickinson (US) LLP

(57) ABSTRACT

The invention relates to a method for designing a dental appliance for a facial skeleton including dental crowns and the roots corresponding thereto, said method including the following steps: producing a volumetric image of the facial skeleton, in the form an initial digital file, using medical imaging; modifying said volumetric image by means of the computer processing of said initial digital file, and obtaining a modified digital file, said modification including at least one tooth movement with a view to implementing a desired correction of the dentition; designing said dental appliance using said initial digital file and said modified digital file, and producing a file capable of being used by digitally controlled machines capable of manufacturing a dental appliance. In the step of modifying the volumetric image, for each tooth that is moved, the crown thereof is individualized and the root corresponding thereto is associated therewith, characterized in that said volumetric image of the facial skeleton includes the image of the mandibular joint and a record of the movements of the mandible over the course of a plurality of movements of said mandible, so as to account for the possible movements of said joint after capturing the movement of said mandible.

10 Claims, 9 Drawing Sheets

Figure 5:
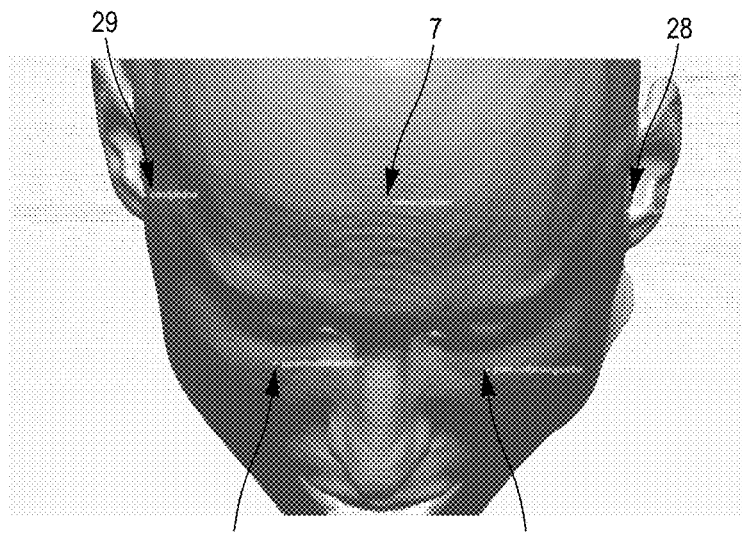

(51) Int. Cl.
  *A61B 5/00* (2006.01)
  *A61C 7/00* (2006.01)
  *A61C 19/045* (2006.01)
  *A61B 5/11* (2006.01)
  *A61B 6/14* (2006.01)
  *A61C 9/00* (2006.01)

(52) U.S. Cl.
  CPC .............. *A61B 5/7425* (2013.01); *A61C 7/00* (2013.01); *A61C 7/002* (2013.01); *A61C 19/045* (2013.01); *A61B 5/0088* (2013.01); *A61B 6/14* (2013.01); *A61C 9/0053* (2013.01); *F04C 2270/0421* (2013.01)

(58) Field of Classification Search
  CPC .............. G06F 19/3437; G06F 3/0484; G06T 2207/30036; G06T 19/003; G06T 17/00; G06T 19/00; G06T 19/20
  See application file for complete search history.

(56) References Cited

U.S. PATENT DOCUMENTS

| | | | | |
|---|---|---|---|---|
| 7,092,784 | B1* | 8/2006 | Simkins | A61C 7/08 433/6 |
| 7,245,977 | B1* | 7/2007 | Simkins | A61C 7/00 433/172 |
| 2001/0002310 | A1* | 5/2001 | Chishti | A61C 7/00 433/24 |
| 2002/0010568 | A1* | 1/2002 | Rubbert | A61C 7/00 703/6 |
| 2002/0176612 | A1* | 11/2002 | Tuncay | G09B 23/30 382/128 |
| 2004/0029068 | A1* | 2/2004 | Sachdeva | A61C 7/00 433/24 |
| 2004/0172150 | A1* | 9/2004 | Perot | A61C 13/0004 700/98 |
| 2006/0095242 | A1* | 5/2006 | Marshall | G06F 19/3437 703/11 |
| 2007/0197902 | A1* | 8/2007 | Schutyser | G06T 7/0012 600/416 |
| 2008/0015727 | A1* | 1/2008 | Dunne | A61B 5/4547 700/118 |
| 2008/0176182 | A1* | 7/2008 | Hultgren | A61C 19/04 433/69 |
| 2008/0182220 | A1* | 7/2008 | Chishti | A61C 7/00 433/24 |
| 2008/0248443 | A1 | 10/2008 | Chishti et al. | |
| 2008/0286712 | A1 | 11/2008 | Imgrund et al. | |
| 2009/0113714 | A1 | 3/2009 | Greenberg | |
| 2011/0207072 | A1 | 8/2011 | Schiemann | |
| 2012/0015316 | A1 | 1/2012 | Sachdeva et al. | |
| 2013/0282351 | A1* | 10/2013 | Tank | A61C 13/0004 703/11 |
| 2017/0065379 | A1* | 3/2017 | Cowburn | A61C 19/04 |
| 2017/0100214 | A1* | 4/2017 | Wen | A61C 7/002 |

OTHER PUBLICATIONS

Röhrle, Oliver, et al. "Using a Motion-Capture System to Record Dynamic Articulation for Application in CAD/CAM Software." Journal of Prosthodontics 18.8 (2009): 703-710.*

Orlanducci et al. "Prothese amovible complete unimaxi aire: les difficultes liees a l'occlusion." Information Dentaire No. 10 (Mar. 7, 2001), pp. 637-651. 13 pages.

* cited by examiner

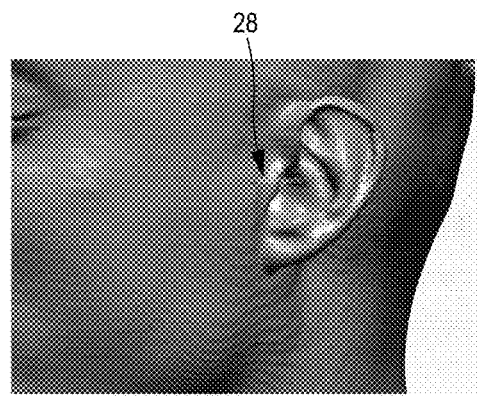
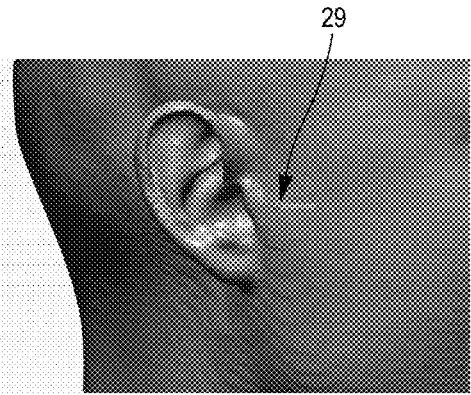
FIG. 1  FIG. 2
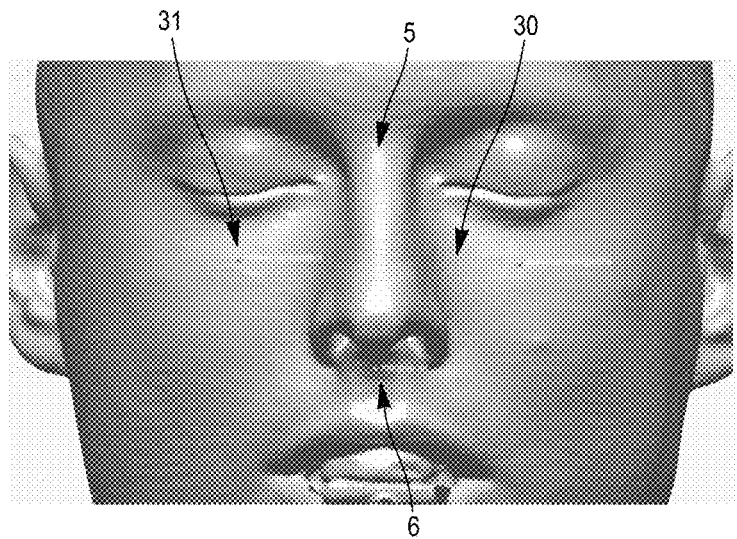
FIG. 3
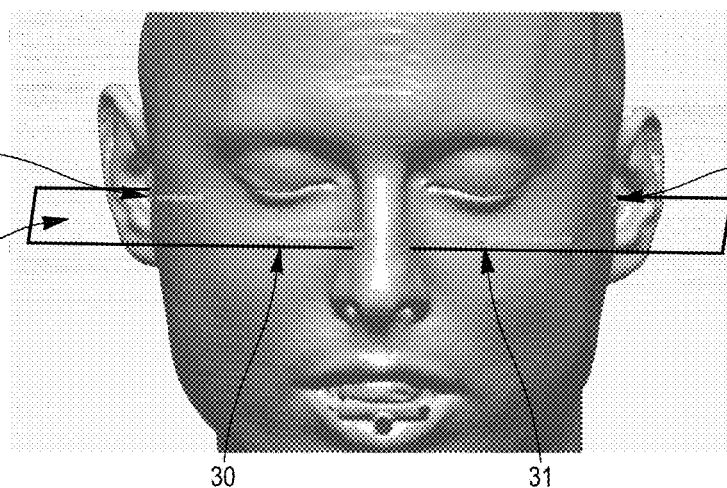
FIG. 4

METHOD FOR DESIGNING AN ORTHODONTIC APPLIANCE

The invention relates to the field of design of orthoses for the correction of dentitions, by dental practitioners.

It relates more particularly to a design process of such orthoses for improving their adaptability and their efficacy.

Orthoses or inter-occlusal devices are fixed prostheses (inlay, onlay, crown, bridge), or occlusal splints, used in muscular (to relax) or articular (to reposition) therapy. A splint is therefore an orthopaedic tool which must ensure return to a functional position. This branch of dentistry is called gnathology. The term dental appliance will be used hereinbelow to cover any object intended to be manufactured and implanted in a dentition, whether to replace one or more teeth or parts of teeth or to be added to the dentition, for example to be fixed above to shift them.

The definition and the positioning of a splint are therefore based as much on a good definition of dental arches, on which it rests, as on observation of mandibular movements.

A CAM (computer-assisted manufacturing) system of inter-occlusal devices within a digital model of the facial skeleton, after capturing of the movement of the mandible combines:

Cone Beam Computerized Tomography or CBCT of bone bases (jawbones), providing an image of the jawbone and therefore of the temporo-mandibular joint cone beam computerized tomography is used in dentistry to obtain an image in three dimensions of the mandible joint, due to low dosimetry and its three-dimensional character: in a single revolution the entire volume to be radiographed is scanned it was the object of evaluation by the Haute Autorité de Santé [French National Authority for Health] in 2009 an optical scanner for obtaining a virtual model of the teeth of the patient a device for taking into account the movements of the jawbone a 3D optical camera capable of marking in space the characteristic points of the facial skeleton, to place the dental arches relative to this facial skeleton.

The inter-occlusal device is then made by powder sintering, or by machining, or even by stereo-lithography.

An orthodontic set-up is completed. A set-up is a simulation of the preferred dental displacement (target state) on completion of treatment; according to the prior art it is obtained by manipulation of a physical model, or can be obtained digitally. However current solutions proposed do not reliably provide all consequences on the immediate environment of the displacement of a tooth.

In the prior art, anticipation of the displacement of roots occurs via physical modelling, whereas their follow-up needs repeated radiographs, or does not occur (hesitancy to undertake imaging examinations in children due to the secondary effects of radiation).

The present invention proposes addressing at least some of the above disadvantages and proposes a solution which more reliably anticipates the effects on the overall dentition of a correction made to a tooth, while limiting exposure of the patient to radiation.

For this purpose, the invention relates to a design process of a dental appliance of a facial skeleton comprising teeth crowns and the corresponding roots, said process comprising the following steps:

constitution by medical imaging of a volume image of the facial skeleton in the form of an initial digital file modification of said volume image by computer processing of said initial digital file and obtaining a modified digital file, said modification comprising at least one tooth displacement in light of a preferred correction of the dentition design of said dental appliance by using said initial digital file and said modified digital file, and production of a file utilisable by numerical control machines capable of manufacturing a dental appliance.

Said process is particular in that in the modification step of the volume image, for each tooth forming the object of displacement, its crown is individualised and the root corresponding to it is combined.

So the process according to the invention is capable of taking into account any effects on the overall dentition and therefore allows obtaining much more reliable behaviour predictions.

According to other characteristics:

said volume image of the facial skeleton can comprise the image of the mandibular joint so as to account for possible movements of said joint; this allows taking into account the various possible positions of the jawbone for the design of the dental appliance, said tooth displacement can be accompanied by the plotting of curves sketching the positioning of the occlusal edges of said tooth and the end position of the vestibular faces of said tooth; this allows easily displaying the effect obtained by the planned correction, said computer processing can further comprise evaluation of the forces to be applied to said tooth to allow said displacement, which allows more reliably anticipating effects on the immediate environment, placing of the dental appliance can be accompanied by placing of a bracket for fixing a shape memory wire and accordingly guide orthodontic traction; this improves the precision of any corrections made, placing of the dental appliance can be accompanied by placing of a bow for assisting the force to be applied to a dental arch, placing of the dental appliance can be accompanied by placing of microscrews implanted at the level of the bone; the position of these microscrews can be determined optimally due to knowledge of the displacements of the roots of the tooth as well as of the adjacent teeth.

The present invention also relates to application of the process according to the invention for correctly replacing one or more misplaced teeth, for replacing one or more missing teeth, or restoring them by a crown or crowns or an inlay or inlays, or for the design of an occlusal orthosis of occlusal liberation or mandibular anteposition.

The present invention finally relates to a design system of a dental appliance of a facial skeleton, specially designed for executing the process according to the invention, and comprising a medical imaging device, and software capable of processing said image by displacement simulations of at least one tooth, and capable of creating a file executable by a numerical control machine for making said appliance.

The advantage originating from the present invention consists of capturing movements improving the definition of the dental appliance, for example of the inter-occlusal device (splint), but it also introduces the possibility of detecting joint pathologies, and treating them prematurely due to splints constructed in CAM, from digital data gathered directly on the patient.

Other characteristics and advantages of the invention will emerge from the following detailed description relating to an embodiment given by way of indication and non-limiting, and to the drawings hereinbelow.

FIG. 1: Placement of the marker on the cutaneous surface objectifying the left condyle FIG. 2: Placement of the marker on the cutaneous surface objectifying the right condyle FIG. 3: Placement of the markers on the cutaneous surface objectifying the nasal spine, the nasion and the two sub-orbital points.

FIG. 4: Frankfurt plane passing through the reference points.

FIG. 5: Intercondyle point. The point is viewed via transparency of the cutaneous surface.

Figure 6:
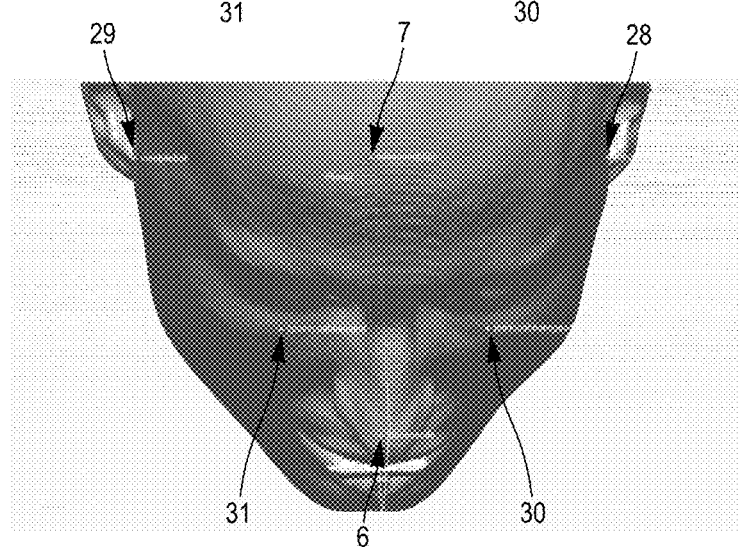

FIG. 6: Median sagittal axis passing through the sub-nasal point, the intercondyle point and perpendicular to the horizontal plane.

Figure 7:
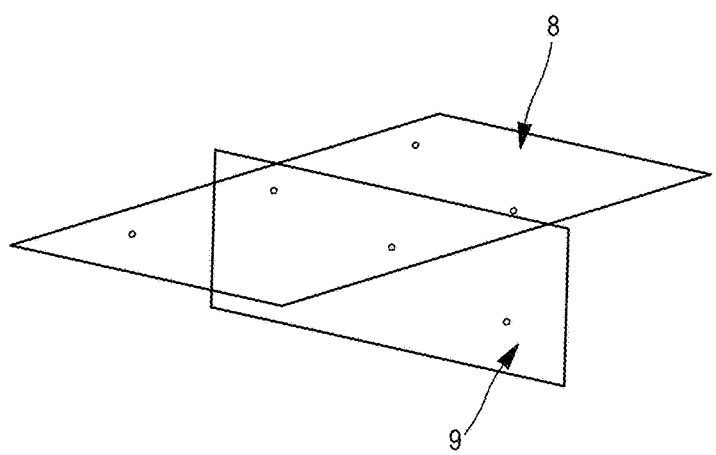

FIG. 7: Axis, points and reference plane detected by the camera and objectified by the software. The dental arches will be located relative to these references.

Figure 8:
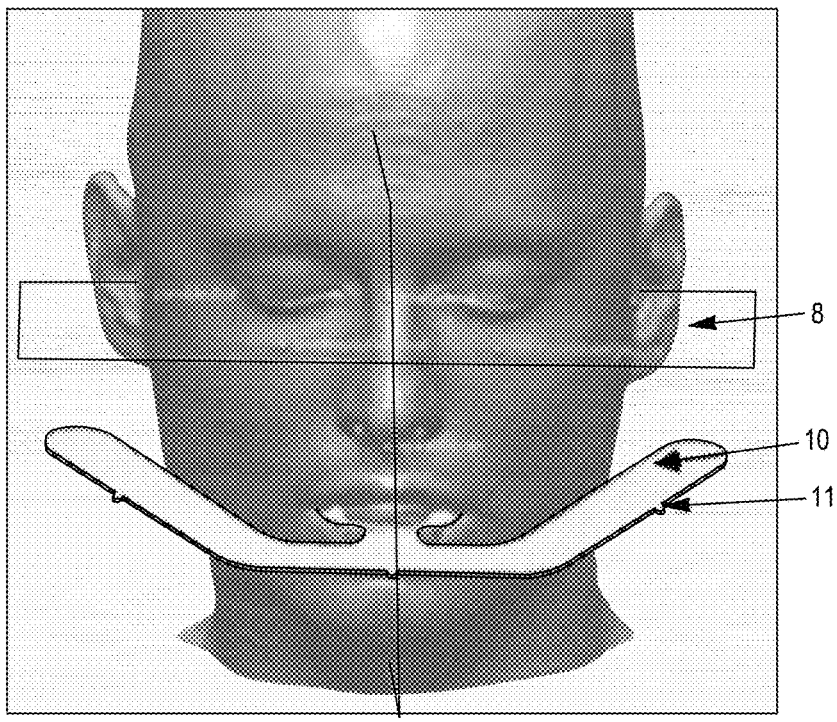

FIG. 8: Type of commercial camera utilisable for the process.

Figure 9:
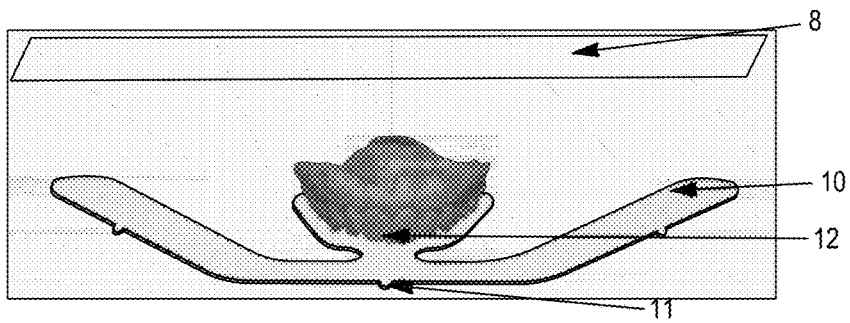

FIG. 9: Fox plane. Our positioning plate is inspired by its design.

Figure 10:
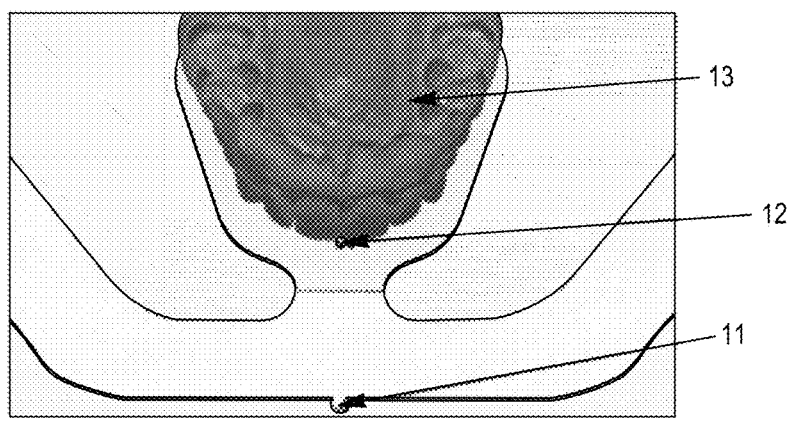

FIG. 10: Plate applied to the upper teeth. Situation relative to the different planes. The markers here in the form of balls can be traced by the camera.

Figure 11:
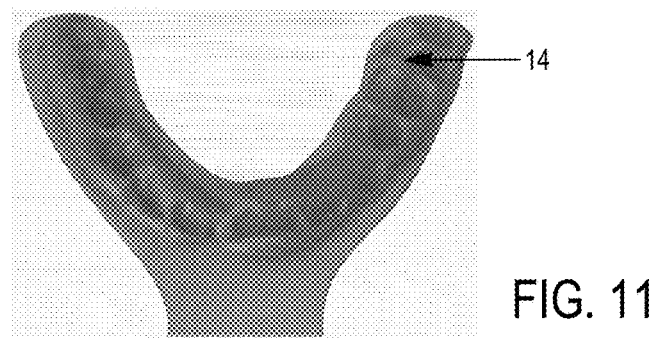

FIG. 11: Exposed view of the ratio between the plate and the maxillary teeth.

Figure 12:
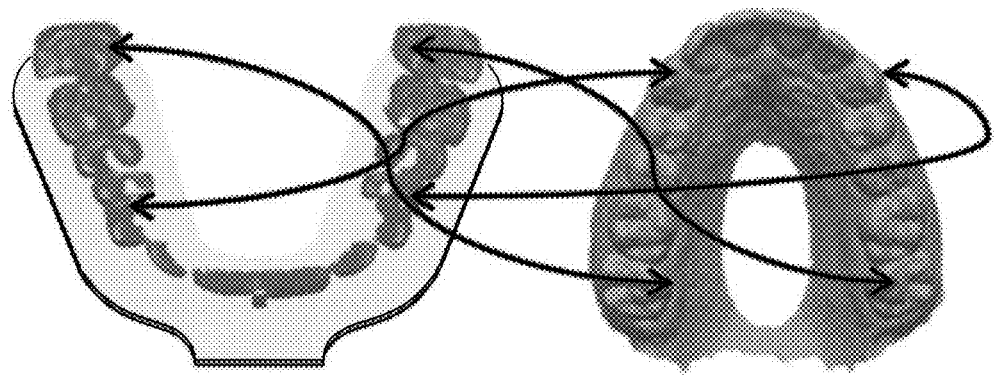

FIG. 12: During placement in the mouth of the plate, the target is placed in the incisive medium. Only the ball mark in front is visible by the camera. As the distance is known between the ball and the target, the position of the incisive medium is then deduced.

Figure 13:
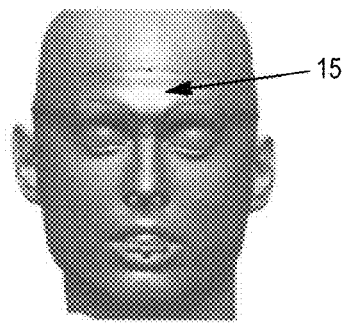

FIG. 13: Imprint left in plastic deformation material on the intrabuccal portion of the plate. This portion is then scanned. The scanner also records the edges of the plate and the geometric markers placed above. Here, an example of table scanner.

Figure 14:
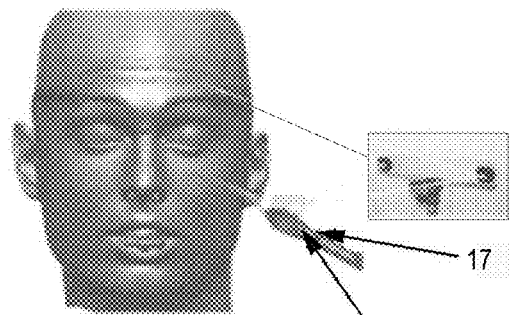

FIG. 14: Correlation necessary to locate the virtual model of the arch on the virtual model of the imprint left by the teeth of the patient on the plate.

Figure 15:
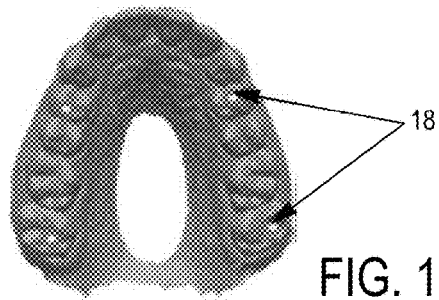

FIG. 15: Points determined on the virtual arch then searched for in the mouth.

Figure 16:
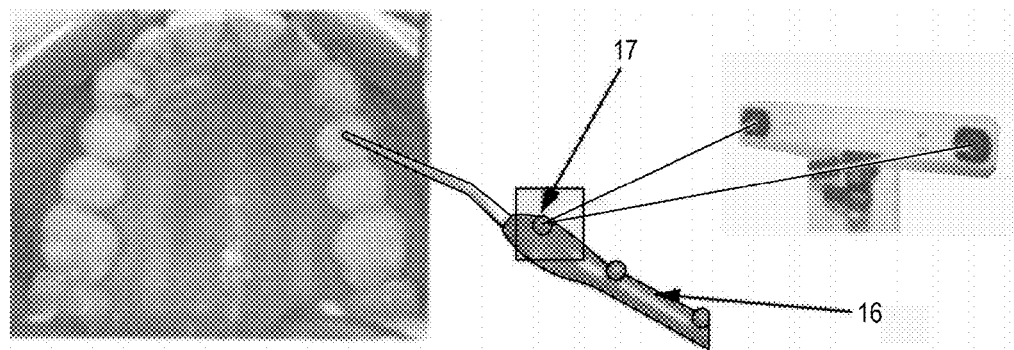

FIG. 16: The stylus is tracked by the camera and clicks on the previously selected points of interest.

Figure 17:
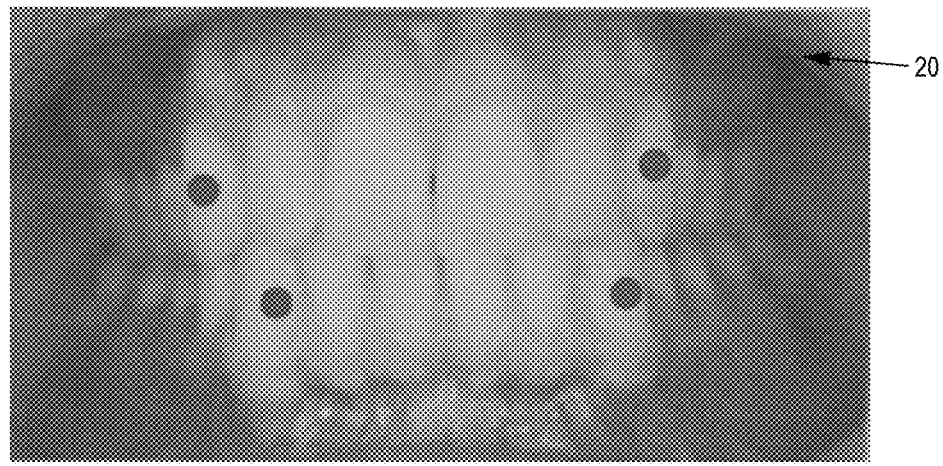

FIG. 17: Example of placement of diodes. A spacer is placed to make the latter visible by the camera. The mandible is set in motion and recorded.

Figure 18:
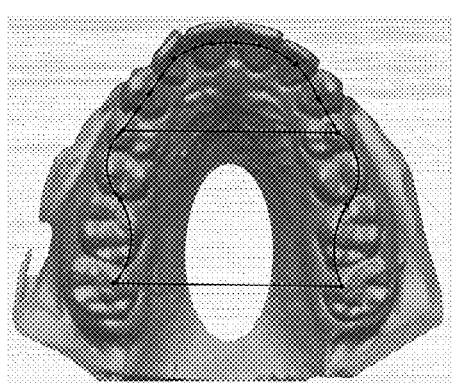

FIG. 18: Marking of cuspid points.

Figure 19:
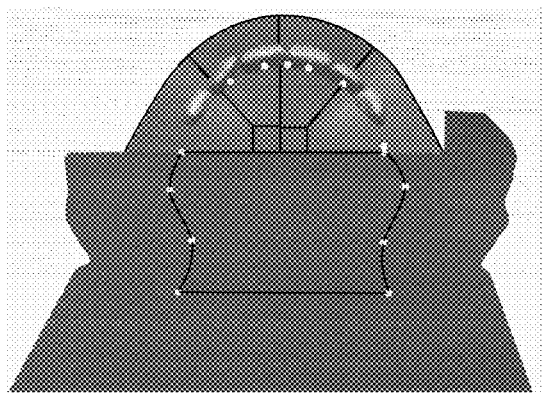

FIG. 19: Creation of the occlusion plane on the antagonist arch.

Figure 20:
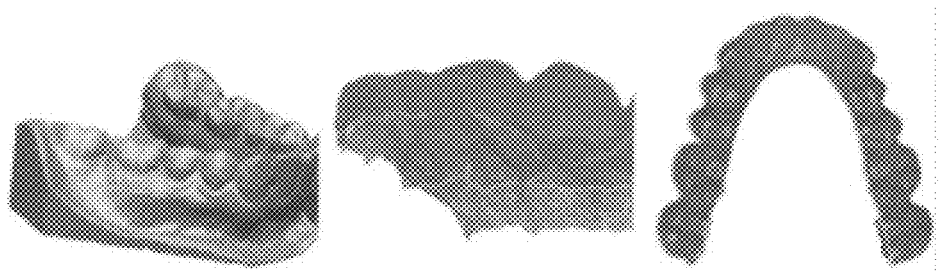

FIG. 20: Duplicates of the meshing for making the surfaces of the splint.

Figure 21:
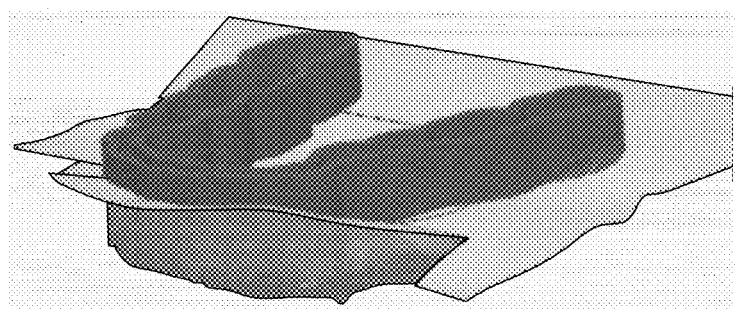

FIG. 21: Section through the maxillary cuspid plane of the extrusion of edges.

Figure 22:
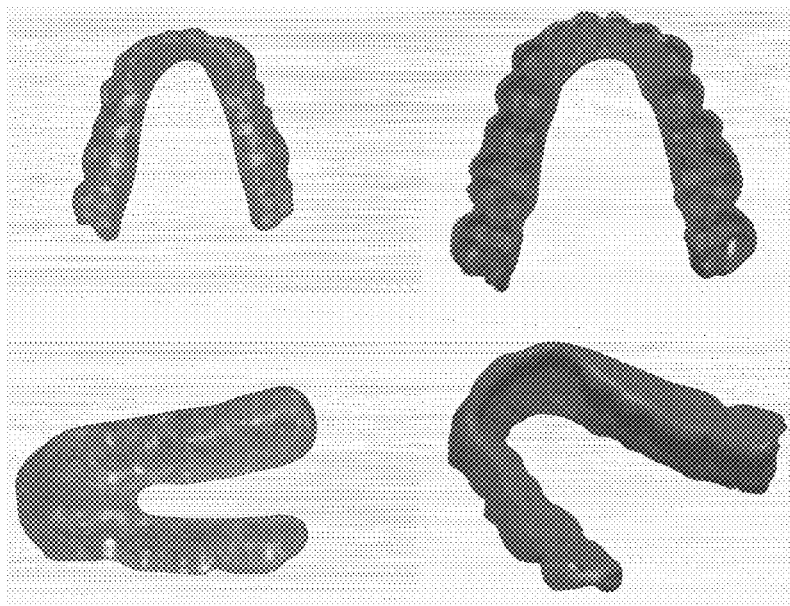

FIG. 22: View of the CAM of the splint.

Figure 23:
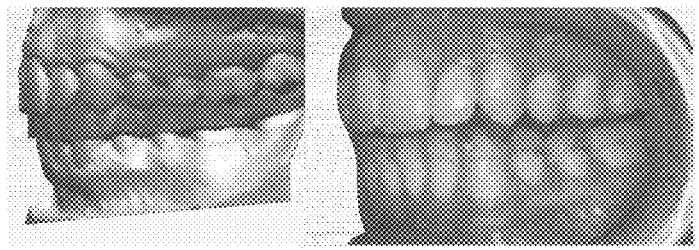

FIG. 23: Adaptation in mouth, perfect and as per the computer project.

Figure 24:
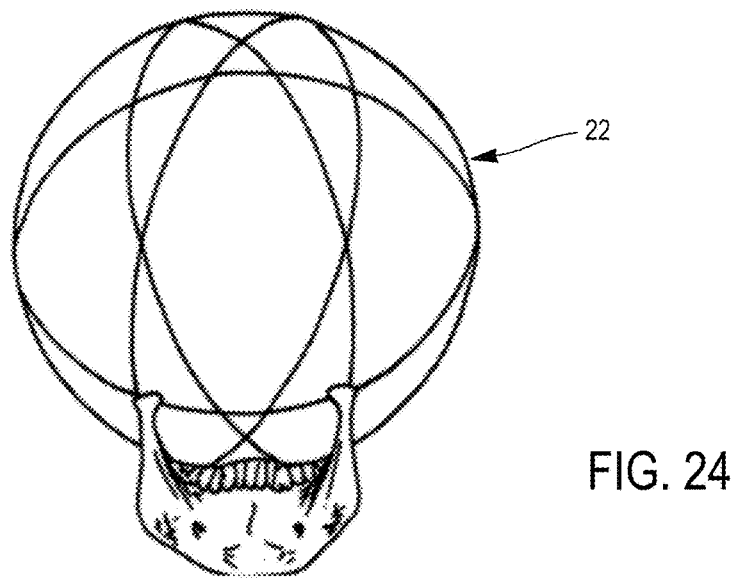

FIG. 24: Monson sphere, according to Orthlieb.

Figure 25:
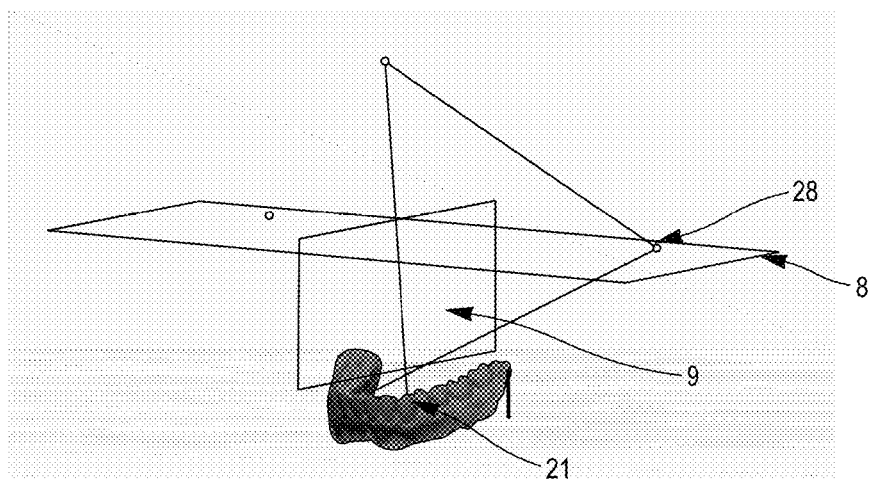

FIG. 25: Carry over of lengths, situation of the centre of the Monson sphere on the median sagittal plane.

Figure 26:
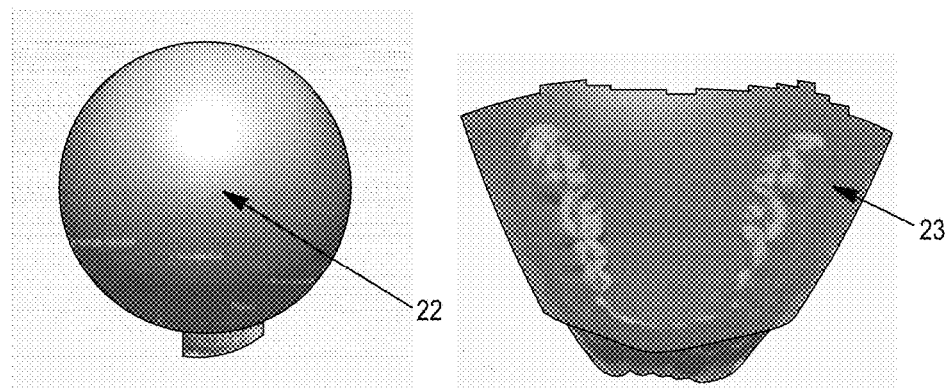

FIG. 26: View of the sphere applied to the mandibular model. Use of a cap to evaluate dental positioning.

Figure 27:
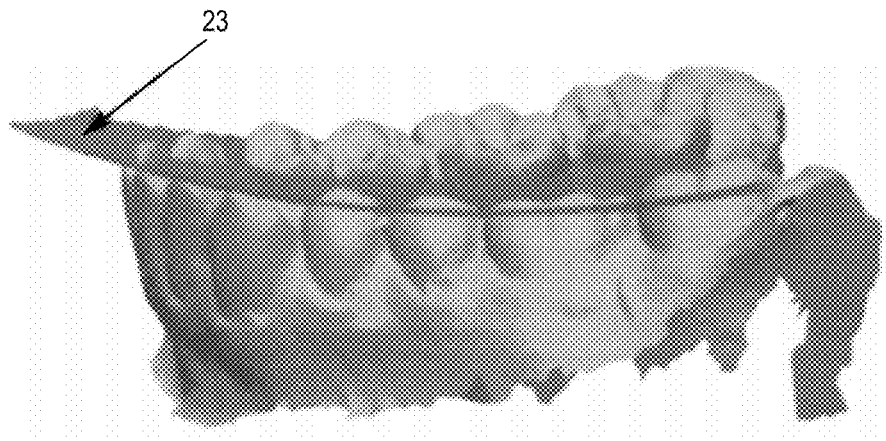

FIG. 27: The resulting anatomical cap gives us the idea of the Spee curve in sagittal view.

Figure 28:
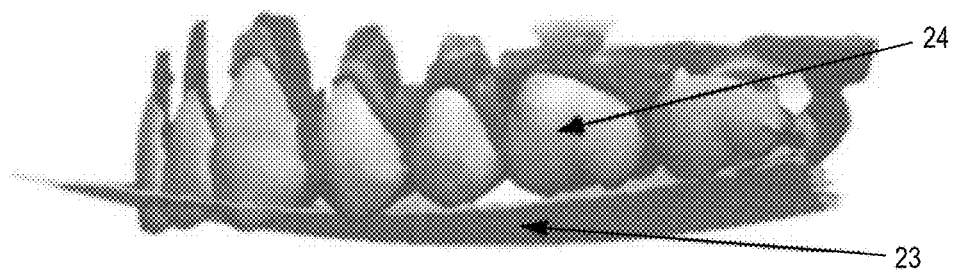

FIG. 28: Situation of a digital set up relative to the "occlusal cap derived from the Monson sphere".

Figure 29:
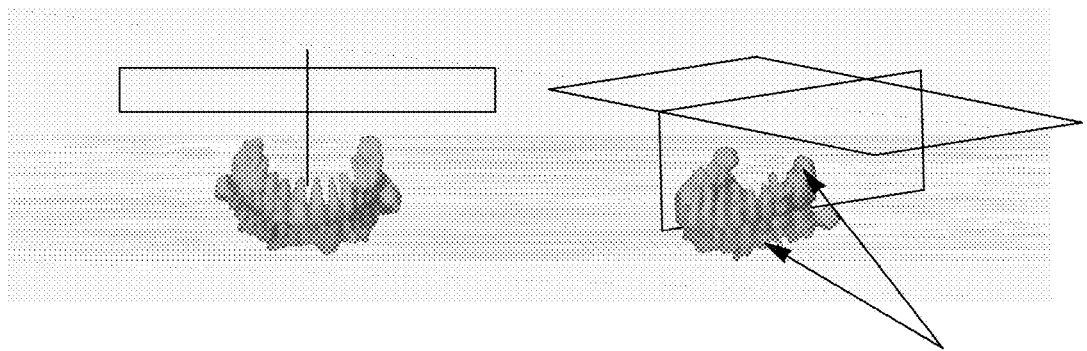

FIG. 29: Importing of root volumes for validating the set up.

Figure 30:
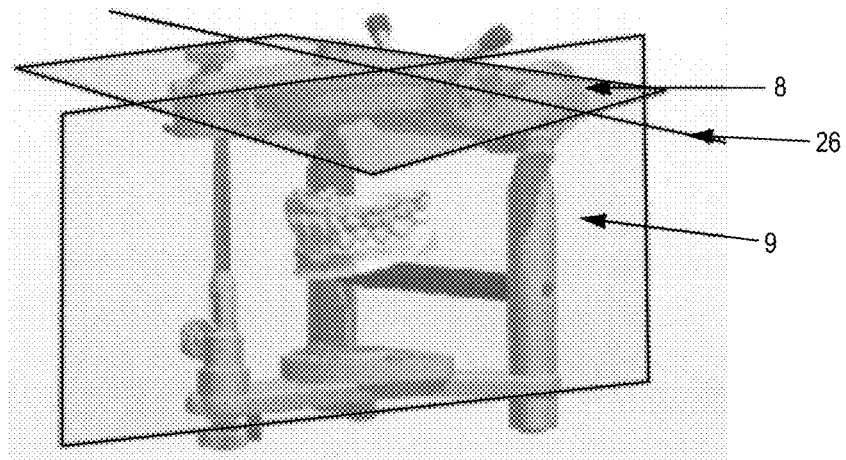

FIG. 30: Correspondence of planes and axis previously determined by the cameras with commercially available articulators in some CAM software. The dental arches already located relative to the latter are therefore easily transferable to the articulators.

Figure 31:
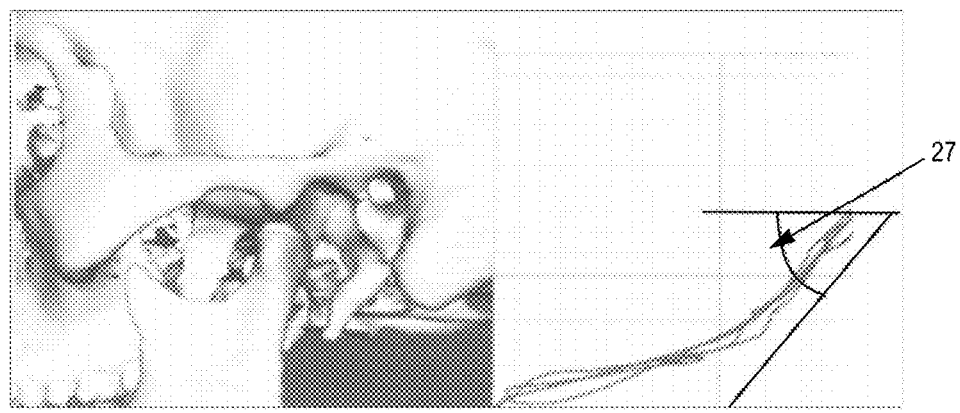

FIG. 31: The software determines the angular values of the articulation. For imaging here, the condyle slope obtained by the propulsion motion. The above software will release only the displacement curve.

Figure 32:

FIG. 32: Adjustable condyle housings which can receive displacement information from the condyle harvested with our system. At left the digital version, to the right the mechanical version.

A CAM system (computer-assisted manufacture) of inter-occlusal devices within a digital model of the facial skeleton, combines:

cone beam computerized tomography or CBCT of bone bases (jawbones), which gives an image of the jawbone, and therefore of the mandible joint an optical scanner for obtaining a 3D view (that is, in three dimensions) of dental arches (all teeth of the jawbone)

a motion-capture device, which records displacements of the mandible and advantageously replaces the mechanical articulator which functions from the plaster cast of the two jawbones and is less precise. This motion-capture device works from reflecting passive sensors, or active ones with sensitive photocells, or on the basis of an accelerometer associated or not in IMUs (Inertial Motion Unit), capturing the movement of the surface on which it is placed, or finally by inertia unit, a 3D optical camera capable of measuring in space the characteristic points of the facial skeleton for placing the dental arches relative to this facial skeleton.

Cone beam computerized tomography produces a 3D view of bone bases for producing a cephalometric study, from which is deduced an ideal position of the teeth at the level of the facial skeleton (skeletal part of the face: there is 3D information on the form and length of the roots and their initial positioning).

An optical scanner produces a 3D view of the dental arches, and the modelling software packaged with the system can merge the <<crowns>> part with the <<roots>> part.

This provides a breakdown view of each tooth and the one-by-one display of teeth, then final set up with the position of each of the teeth in its environment, then intermediate models, whereas the software quantifies the displacement of each tooth provided by orthodontic treatment, in three directions.

The interest of this three-dimensional modelling is to be able to guide the orthodontist in his therapeutic choices: the necessary forces to be applied to the crowns to obtain displacement over time can be calculated exactly.

In addition, in the case of setting microscrews, to reinforce anchoring, modelling allows placing these cortical anchorings without the risk of telescoping with the roots and their displacement during treatment.

The tomodensitometric data of patients can be obtained by means of any medical scanner. The practitioner who does not have a cone beam in his clinic can send his patient to a radiologist who will provide him in return with the scanner images in DICOM format (Digital imaging and communications in medicine: standard for information management of data from medical imaging). But it is in the interest of the practitioner to have his own Cone beam scanner. Already for a low rate of rays this generates for the patient but also for practical reasons, to keep the patient in the clinic. Also for time gain and reducing costs, the number of collaborators should be limited.

The process according to the invention is capable of merging the 3D model of the dental arches of the patient with the 3D data of the facial skeleton of the patient coming from the scanner. There are two possibilities for this:

It is possible to see the dental prosthesist if the latter has a 3D optical scanner. The practitioner must previously make imprints of the arches by means of plastic deformation material. He then recovers the digital file from the dental arches after sending this imprint to his prosthesist.

But as mentioned above, it is in the interest of the practitioner to have a tool for digitising dental arches. Currently on the market there are enough offers of this technology for the dentist to be able to find what suits him. The most attractive solution is to have an optical intrabuccal fingerprint camera on the chair.

As indicated above, the aim is to obtain displacement data of the mandible over time and in space. This information can come from different systems such as:

modern electronic axiographs which transform movement into digital data integrable into software optical cameras which follow displacement of markers placed on the surface of the teeth displacement evolution between several sensors distributed at the level of the upper and lower dental arches. The sensors used are inertial sensors or accelerometers.

The displacement information is then processed by the 3D model.

The software will process all the data contributed. This is both cephalometric analysis software, and modelling and surface-rendering software. It is also software which materialises treatment by the bracket design by CAM and aids the practitioner in operating his treatment orally.

Now follows a step-by-step description of handling the input data and of the way in which they are analysed and processed in the software:

Cephalometry comprises a set of techniques for measuring the head and is necessary for orthodontic diagnostic. The practitioner draws conclusions therefrom in relation to a possible defect in dental positioning, but also a defect in growth of maxillary bones.

Tomodensitometric data can be read in 2D (two dimensions) and cephalometric study can be done accordingly. The points of interest necessary for calculation of angles between the different reference planes are situated there. But the interest is to call on volume tomodensitometry and apply a process of volume cephalometry. This also offers the possibility of revealing possible defects in growth of the transversal direction. In all cases the process according to the invention is necessarily based on 3D modelling of the facial skeleton. The software utilises data originating from imaging in the DICOM format to recreate in 3D a virtual representation of the cranium. At this stage it is necessary to individualise the mandibular bone from the maxillary as well as the dental roots of the alveolar maxillary bones and more precisely the teeth with their roots. The marker points are located on the 3D volume of the cranium, then the software supplies information in the form of values on dental positioning or positioning of maxillary bones relative to the base of the cranium. These data are based relative to normality defined by the authors having carried out this type of cephalometric analysis. The ideal position of the teeth is known and used throughout operations.

Next comes a step for creation of fully digital set up, with consideration of the root volume.

This step flows on from the preceding analysis. The technique to be described hereinbelow is particular to the process according to the invention and is found in no other software.

The file of the digitised dental arches originating from the optical scanner is imported. Next, this 3D model has to be combined with and correlated to the forms of teeth obtained by means of the tomodensitometric examination. This is necessary as the arches obtained by the optical system have better definition. Each crown of the teeth on these arches is individualised and they are combined with the roots corresponding to them. Each crown root unit is then ideally shifted by means of a <<Trackball>> (software tools for shifting a 3D object spatially) based on and relative to the cephalometry results. Another function for shifting teeth is planned. 3D curves sketching the positioning of occlusal edges of teeth as well as the end positions of vestibular faces of teeth are drawn. The inter-incisive medium is also placed. Reference points are located on the teeth and these merge with the curves determined previously. Adjustment via the Trackball is then performed to best place the roots within the bone bases but also to prevent root proximities. The anticipation of dental displacements by means of this set up, a veritable simulation of final treatment, manages the applied forces to prevent bone fenestrations.

The process according to the invention proposes designing multi-ring and multi-attachment appliances. The proposed technique for placing can be a vestibular technique or a lingual technique. The appliance comprises different elements. Our process offers total or partial aid in their forming.

The brackets are artifices stuck to the surface of the tooth. Their role is to fix the shape memory wire and guide the orthodontic traction. Both the design and placement on the tooth are handled by the CAD (Computer-Assisted Design) software. Each ring or attachment is fitted with a throat into which a metal wire or orthodontic bow is slid. It is this bow which guides displacement of the teeth. The orthodontic rings, placed correctly, shift the teeth with a high degree of precision. This CAD is then entrusted to numerical control machines to ensure their manufacture. The technique can be placing the printed bracket into castable wax, or machining via robot micro-milling or even shaping via micro-fusion of metal powder technique.

The bows: they are selected as a function of the arch perimeter but also of the force to be applied. The therapeutic project in the form of simulation or set up more easily guides our choice relative to the dimension of the bow but also its force to avoid secondary effects such as rhizalyses or bone fenestrations. Once the adequate bow is selected we propose virtual folding to be then entrusted to a robot which will ensure automatic folding.

Microscrews: to augment the anchoring, we sometimes use microscrews implanted at the level of the bone. Our software favours placement of these microscrews since the final position of the roots is known by means of simulation. For implanting, the experience of the dental surgeon can suffice, otherwise we propose designing surgical guides, a type of small splints to be placed on the surface of the teeth and pre-perforated for guiding the hand of the surgeon who will screw these microscrews into the bone.

The process according to the invention relates to restorative dentistry and occlusodontology. We are interested mainly in processes for collecting the mandibular kinematics and its reproduction.

Existing major systems for follow-up of mandibular displacements on the market are nothing more than an evolution of mandibulographs launched in the fifties. These systems fixed to the mandible of the patient objectify the displacements in space of this mandible. Plots of these displacements are obtained and then analysed to diagnose articular pathology or even to program a simulator of mandibular kinematics. The dental arches of the patient are placed on these simulators, allowing the practitioner and prosthesist to conduct diagnosis and then to make prosthetic artifices or occlusal orthoses. These works are then placed in the mouth of the patient to re-establish a manducatory function which is deficient due to loss of teeth or to support muscles or a painful joint by means of the occlusal orthosis.

Our project is innovative on several points. First, this effort commences by collecting the mandibular kinematics until the design of prosthetic artifices is entirely dematerialised by means of digital technologies. This is done by combining the data supplied by different technologies such as motion-capture devices, X-ray medical imaging as well as 3D imaging obtained from optical scanners. These data are then processed and assimilated into the software, then the prostheses and orthoses are made by numerical control machines tools.

We will now describe the handling of the interface to understand its operation.

We can use the software of the process according to the invention in different ways as a function of the result we want to get.

We can use it as a functional occluder, that is, combining 3D dental arches with a motion-capture device.

We utilise this function:
When we want to replace missing teeth or restore them using crowns or restore them using inlays/onlays. The position of markers recording displacement must be found commonly between the 3D models of the arches and their real situation in the mouth. This is done by way of physical or optical imprints. Knowledge of the evolution of the position of sensors or markers in space is applied to their virtual graphic representations now attached to the dental arches. This is how we obtain the motion of the virtual arches. This function is applicable only in some clinical situations. The presence of functional dental guides is necessary. In this case, displacement of the mandible is under the influence of the remaining teeth. We have no need to take into consideration the articular morphology.

CAD work on prosthetic pieces is done such that the occlusal morphology integrates perfectly in functional space offered by mandibular kinematics. The occlusal morphology of our restorations is optimised and integrates without causing discomfort.

When we want to design an occlusal orthosis of occlusal liberation or mandibular anteposition. We place the mandible of the patient in the reference position and the displacement data are transmitted to the 3D models. The computer-assisted design of the orthoses interposed between the arches is now possible. Computer-assisted manufacture is undertaken by means of numerical control machine tools. This avoids having to mount the physical models on a mechanical simulator.

We can then use the software as a physiological Articulator:

In some situations, we try to comprehend the operation of the joint because it contains the history of the mandibular kinematics especially when we have lost any occlusal information. The design of our future prostheses must be based on articular morphology so as to avoid creating interference and prematurity likely to injure the joint.

For this to happen, the data of movement acquisition have to be applied to the virtual model of the mandible of the patient. As explained previously volume tomodensitometry is necessary for modelling bone structures. The software comprises an algorithm for isolating the mandibular bone from the base of the cranium. The radiographic examination can be conducted with the acquisition system in the mouth. The markers or emitters of the mocap system (motion capture, for motion-capture devices) have to be modelled at the same time as the mandible. The displacement measurements are then applied to the virtual representation of the markers. The virtual mandible is then set in motion. A single radiographic examination is necessary. It is possible then to make as many movement acquisitions as wanted provided that the markers or sensors are placed in the same situation as originally. A slight variation can be tolerated since calculation by rigid transformation is put in place in the software. The acquisition of the movement must commence mandatorily in the same reference position as that used during the radiographic examination.

The virtual dental arches of the optical scanner are then correlated on the model originating from the tomodensitometry. The CAD of the restoration works and the occlusal orthoses is done by displaying in parallel the evolution of the intra-articular interlining, a gauge of the good health of the Temporo Mandibular Joint (TMJ).

We can finally utilise the software as a TMJ recorder.

This function needs the same handling as previously but the models of the arches are not integrated as only the mandibular kinematics are of interest. The interest is principally diagnostic but can be also therapeutic in recoaptation condylodiscale manipulations.

When the dental organ is degraded, the role of the dental surgeon will be to restore it. In the event of major disrepair, he will have to use prosthetic artifices replacing all or part of a tooth or teeth concerned. This cannot be done without taking into consideration dental occlusion which is the way in which interdental and inter-arch contacts are organised. But it is not just situations or management of dental contacts which are a therapeutic imperative. For example, orthodontic treatment is undertaken when the teeth are in an ectopic position. The teeth are shifted by means of an appliance. The schema and the distribution of occlusal contacts change and rules are to be respected in this case so as not to injure the patient. In other cases, when disorders of the joint or muscular contraction are diagnosed and relate to occlusion, the dental surgeon can attenuate or even correct these dysoperations by the design of an occlusal splint.

By extension, occlusion ensures an interface between the two maxillas. Their confrontation is possible by means of a mobile bone: the mandible (lower maxilla). The quality of this occlusion is essential and must ensure 3 essential functions <<Centring; Wedging; Guiding>> of this same mandible to preserve the surrounding structures (joint, muscles . . . ). This motility is therefore due to a joint, the temporo-mandibular joint (TMJ) and setting in motion by contraction of masticator muscles. At any time, the dental surgeon is mindful of preserving the good health of these components but also its reestablishment. In fact, when pathologies are objectified (myalgia, arthropathy) by way of rehabilitation of occlusion the dental surgeon can have a retroactive effect on the pathologies of the manducatory tract.

Construction or reconstruction of the occlusion is under the influence of some determinants. These are data linked to the individual having an influence on occlusal anatomy. They are important to obtain in some situations since the prosthesist will be inspired to model the occlusal surface of the teeth. In this case there are tools available known as articulators which more or less try to reproduce the physiology of the manducatory tract.

To better understand the process according to the invention we will succinctly describe the determinants of occlusion and place its application in opposition to other systems available on the market. The innovation flowing from this manufacturing process should be proved.

The determinants of occlusion are defined as follows: it is the factors which can be classified of the manducatory tract which influence occlusion. These factors are divided into two groups: those which are fixed and those which can be modified by remodelling or repositioning of teeth. The most cited fixed factors are intercondyle distance; anatomy of the temporo-mandibular joint, which influence mandibular kinematics; positioning of the maxillary arch, and intermaxillary relation. The most cited modifiable factors are the shape of the teeth, position of the teeth, vertical dimension, occlusal curves, height of cuspids, and depth of the pits.

These determinants are interdependent on each other. As the modifiable factors are those concerned by rehabilitation work of the dental surgeon, the approach will be in focussing on other fixes and controlling them.

The fixed determinants can be listed as:
1. Vertical and horizontal positioning of the arches relative to the posterior determinant
2. Condyle spread
3. Anteroposterior positioning of the arches relative to the articular posterior determinant
4. Posterior articular determinant:
   a. Condyle slope
   b. Bennett angle
   c. Initial Bennett movement As a function of their sophistication, simulators available on the market control these determinants more or less well. This at the cost of fastidious programming, originating from costly handling over time and source of error in the dental clinic. Also, the role of integrating some of these parameters (2, 3, 4) is to reproduce the mandibular kinematics. This reproduction is just an approach of real mandibular movements since the anatomy of the temporo-mandibular joint is reduced to addition of angular values sketching the trajectories of the mandibular condyle in the planes in space. This is materialised mechanically at the level of the condyle housings of the simulator.

The process according to the invention is innovative on these points. Integration of the determinants is done more simply and intuitively. Especially concerning reproduction of the kinematics. We propose veritable recording of the latter. Once integrated in the software it will be replayed at will to animate the digital models of the dental arches. We could well dispense with harvesting the determinants (2, 3, 4) but this makes our process compatible with existing systems on the market. Concerning information supplied by the position of the dental arches in space relative to the joints and facial skeleton (1), the interest here is studying (in the case of occlusal analysis) and reconstructing the occlusal curves. These curves, the SPEE curve and the WILSON curve, qualify intra-arch organisation. When simplified, these curves correspond to the way in which the occlusal surfaces of the teeth are oriented, their cuspids and the incisive edges in space. This makes us aware of the possibilities of distribution of forces and interarch junction. From this follows analysis on the individual form of each tooth, its own anatomy, depth of the furrows, cuspid height, and its own position relative to the other adjacent and antagonist teeth.

Novel digital technologies to date offer unequalled possibilities for treatment and analysis and we have pushed to develop different clinical protocols. These protocols apply in the various clinical situations cited previously which we will recall during their descriptions.

These protocols are described by three different technologies.

The first technology is an optoelectronic tomodensitometric camera used to retrieve positioning in space of active diodes, small markers sending out a signal.

The second technology is an infrared camera comprising a light source emitting a continuous signal of small infrared points. This signal is then recovered by a small integrated camera. A triangulation method is applied to determine the position in space of the reflecting surface.

The third technology is electromagnetic. The markers are coils giving information according to six degrees of liberty of their position. A source is placed to the side and emits an electromagnetic field.

The present method does not describe the design of the cameras but their uses for positioning the digital models of dental arches relative to reference points characterising the skeleton of the face. This is a step necessary in the design of prosthetic artifices, occlusal orthoses, or even in the planning of orthodontic treatment for making the orthodontic appliance. This method is also useful during all steps of occlusal analysis.

The protocol is divided into different steps slightly variable as a function of methods:
  Placement of markers, reference points: Cutaneous markers and others extrapolated by the software are positioned at the level of the reference zones characterising the facial skeleton of the patient. This also enables management of the determinant 2.
  Determination of planes and reference axis from reference points: A horizontal plane, a sagittal median plane, the bicondyle axis of <<rotation>>
  Situation of dental arches relative to these planes. Management of determinants 1 and 3
  Study and recording of mandibular kinematics. Determinants 4

I. Placement of Markers.

Out front of the tragus to right and left, points corresponding to the condyles. FIG. 1 illustrates the left condyle 28, and FIG. 2 the right condyle 29.

On sub-orbital points 30, 31, by palpating the bony rim under the eye, to the right 31 and left 30.

Place a point of colour, a diode, a reflecting marker or an electromagnetic coil under the nose corresponding to the nasal spine 6 and/or on the point-nasion line 5.

II. Determination of Reference Planes from Reference Points

Create the horizontal plane, the Frankfurt plane 8, reference plane which represents the base of the cranium (it will correspond to the upper branch of the articulator). The plane passes through the two condyle points 28, 29 and the sub-orbital points 30, 31

Next, situate the median sagittal plane (it will correspond to the median symmetry of the articulator).

Calculate the intercondyle point 7 located at the centre of the two condyle points. A computer algorithm determines the spatial position of this point based on the positioning of condyle points viewed by the camera.

Take the sub-nasal point or the point-nasion line, the sagittal plane 9 passes through one of the point-nasion lines 5 or sub-nasal lines 6, and the intercondyle point 7, and is perpendicular to the horizontal Frankfurt plane 8.

These positioning approaches of reference points are identical irrespective of the technology employed to record the position of the markers.

III. Situate the Position of Dental Arches Relative to these Planes a. First Solution: Use of the Infrared Video Camera.

A positioning plate 10 is modified with calibrated markers (here in the form of balls 11) to objectify the position of maxillary teeth relative to the planes: Frankfurt horizontal 8 and sagittal 9.

A positioning marker 12 locates the incisive medium. It is objectified in front on the plate by a ball 11 or another form easily marked by the camera.

By way of reminder, the preceding images originate from modelling but correspond to clinic situation.

Next, the aim is to record with plastic deformation material 13 the placement of teeth on the intrabuccal part of the plate. This portion is dissociable from the extrabuccal part to be scanned. An interincisive target 12 makes positioning easy and contributes other information. The distance between the interincisive target 12 and the ball marker 11 is parameterised and known from the software. As the camera can mark the external element only, the software could define the incisive point.

The plate comprises two separable parts as its dimensions disallow it to be scanned. The plate and its two parts have known dimensions integrated in the software. During 3D acquisition of the imprint 14, the scanner also recognises the edges and markers on the intrabuccal part. The situation of the extrabuccal part is therefore deduced. Once the camera has detected the extrabuccal markers the assembly is therefore placed in space relative to the above planes.

It is then possible to place on the scan of the impression 14 the digital model of the maxillary model by correlation between the forms (see FIG. 12). The orientation and position of the maxillary relative to the base of the cranium, but especially relative to the two condyles 28, 29, is then determined. The digital model of the mandibular arch then contacts the maxillary model, and we will not develop the means for placing in intermaxillary relation.

Advantages: This camera is a veritable scanner by means of its depth sensors capable of transcribing a cloud surface of points to which is attached a RGB camera for adding the texture to the 3D object. The aim is to have available the cutaneous environment of the lips during reconstruction of teeth of the anterior sector. The virtual prosthetic project of interest in the anterior sector will be done as a function of the edge of the lips to locate the smile line.

b. Second Solution: Use of the Optoelectronic Active Camera with Active Diode Recognition.

Another type of camera can be used to localise the position of the maxillary arch and as a consequence the mandibular arch. It spatially marks active diodes. The protocol for determination of the planes and reference points is slightly different. The system comprises a small stylus of calibrated dimension and surmounted by three small diodes enabling triangulation and its tracking in three dimensions by the camera. The aim is the same: to be able to place the digital model of the maxillary model relative to the planes and reference points characterising the facial skeleton, as are the veritable arches of the patient relative to the bone skeleton. Orientation and position are obtained.

First Step:

Placement of the Headband 15 with the Diode Housing on the Front.

This housing is the positioning reference point determining all the following steps. It is placed onto the front of the patient and is held by a headband. A nasal support system also ensures stability. Three diodes minimum distributed over the surface are visible by the camera any time.

Second Step:

Pointing of Characteristic Points of the Face

This step determines the positioning of reference points and planes cited earlier. It is not necessary to apply active diodes to the skin of the patient. The use of a stylus 16 is enough to prick the points on the face of the patient. Recording these points constitutes volume image of the facial skeleton. A button 17 on the stylus clicks to validate the position of reference points each time the end of the probe is in place on the corresponding anatomical points. The stylus is designed such that the software determines the position of the point in space when the camera tracks the diodes placed on the sleeve. At each click, the reference points are fixed in the reference point of the housing frontal. During acquisition immobility is required of the patient. But on completion of <<picking>> movement of the head is no longer a problem. If the head does move and therefore the housing moves, rigid transformation is applied to the different points to retain their position relative to the facial volume.

Third Step:

Pointing of Points on the Maxillary Arch

The points 18 to be found are placed randomly on the 3D model and this also concerns a partially toothed arch, with prepared teeth or implant abutments or even a toothless arch. The imperative here is to place the tip of the stylus in the mouth at the same places as on the virtual model.

The selected zones 18 are zones which ensure stability of the end of the marker. Here the pits of the teeth are selected.

The stylus 16 placed in the mouth has its sensors 19 tracked by the camera. With each click, the position of the target points is viewed by the camera relative to the frontal housing. When the points to be clicked as selected on the 3D model have been located and validated by the stylus, the 3D model takes its place relative to the reference point. Once the previous operation has ascertained the situation of the planes and reference axis relative to the housing the position of the maxillary relative to the reference plane is deduced. In the same way, the 3D model of the maxillary follows the movements of the housing solid with the head.

Fourth Step:

Recording of Kinematics

The static position of the mandibular model relative to the maxillary was recorded previously in the mouth by an intrabuccal optical camera or at the level of a table scanner in the laboratory. At this step the mandibular model therefore finds its place at the level of the base of the cranium and more particularly at the level of the planes and reference axes characterising the latter. The way in which the mandible moves in space has to be known. The principle is the same as previously. Markers are placed solely on the mandibular teeth. The camera will ensure tracking of diodes placed on the frontal reference point and that of the diodes solid with the mandibular arch in motion. The model of the maxillary arch and the reference planes are linked to animation of the mandible in motion. For this to happen, housings containing diodes are distributed and fixed on the mandibular arch. The optical impression serving to restore the mandibular arch in 3D is taken at this moment, the diodes in place (minimum 3). The 3D model includes two items of information:

The form of the arch and all the elements comprising it (for example, occlusal anatomy of remaining teeth, prepared teeth, implant abutments, toothless sectors . . . )

3D rendering of diodes placed on one of these elements.

A correlation is then made between the movements of physical diodes captured by the camera and their modelling. This process is necessary to set in motion the modelled arch 3D. Buccal spacers 20 are put in place to show up the diodes by the camera (see FIG. 17).

In some cases the diodes can be placed in a buccal situation to make mandibular kinematics easier. They are carried at the end of a rod of known size. This rod nests in a reproducible fastening fixed to a portion of the arch. The scanner of the arch is done identically as previously, except that there will be no 3D rendering of the fastening system. But the camera will collect displacement of diodes placed on the rod at a distance from the fastening system. The distance between the diodes and the fastening system is known and invariable. Correlation between displacement of the diodes and the virtual arch is possible.

Additional Functions

Other markers are useful for respecting the rules of aesthetics. The bipupillary line and the rim of the lips are elements on which the practitioner can rely to select the length of teeth of the anterior sector or even select the smile line (of the teeth). Continuous scanning with the stylus on a surface reproduces in 3D this surface in the software Drawing function of the lips by scanning with the stylus. It is possible to ask the patient to smile, to then fix this smile by means of this method. Then, during modelling of front teeth to be reconstructed, the 3D volume of the lip serves as guide.

Bipupillary line. As in the step for determination of planes, the point of the stylus is placed facing the eyes and a click is made in front of each of the latter. The line is traced and it will lend an added source of information to respect a certain parallelism of the occlusion plane and the line of the smile relative to the bipupillary line.

c. Third Solution: Use of Magnetic Markers

This system can be used both to determine the planes and reference points but also to conduct motion capture. It comprises a source and sensors.

The source contains electromagnetic coils enclosed in a moulded plastic shell, which emit magnetic fields. The source is the reference position of the system for sensor measurements.

The sensors are electromagnetic coils enclosed in a moulded plastic envelope and detect magnetic fields emitted by the source. The position and orientation of the sensors are measured with precision when displaced. The sensor is an entirely passive device.

IV. The Resulting Data can be Utilised in Various Ways a. To Place the Models of Dental Arches on Our System with its Own Algorithms The first step was to determine the static position of the arches. The plate comprising its two parts allowed us to do this as for the active diode system and its pointer stylus or the magnetic transmitters. The aim must then be mandibular kinematics.

i. Study and Recording of the Mandibular Kinematics

So that our system is utilisable, it is necessary to animate the mandibular model relative to the maxillary model. Capturing of the movement of the mandible is essential in this case. Two to three markers are placed on the mandibular teeth. Now, it is necessary to add to the maxillary arch since the latter, solid with the cranium, can be subjected to parasite movements due to micromovements of the latter even if the patient is asked to remain still. Rigid transformation is applied any time to transfer these micromovements of the head to those of the mandible, and compensate these involuntary movements, to simulate perfect immobility of the head. The cutaneous points are not used in this case as the skin is slightly mobile under the muscular action of mastication.

The camera has no sufficiently major definition so that we can simply rely on the transmission of the movement obtained in the mouth on the digital model of the mandible. In this case, the software, via another rigid transformation, applies the motion of the markers fixed to the mandibular teeth to the virtual points materialised by the markers located opposite the condyles. The plot obtained is rich in information as it characterises the motility of the temporomandibular joint (TMJ) and can therefore be useful for diagnosing articular pathologies often manifesting by anarchic movement. The other important point is that we can derive therefrom angular data (Bennett angle, condyle slope, lateral displacement giving an indication of the form of the joint. These data are also transferable to commercial simulators (indication developed below) whether virtual or physical. The form of our prosthetic restorations will depend on this.

Since the envelope of movements of the joint is known, it is reused for setting in motion the mandibular model. A detection algorithm of collisions between the two models is integrated into the software. It first prevents penetration between the two meshings but also marks in colour code the intensity and contact zones between the teeth. To mobilise the model, it suffices to click on a point of the meshing and move the mouse to set it in motion.

ii. Part of the Software Also Comprises a Proprietary CAD (Design Computer-Assisted) Part.

The first functions concern the design of the occlusal splint.

1 Making the Splint (Occlusal Orthosis) by CCAM

Modelling of the Occlusion Plane or Cuspid Plane

Selection of the highest points of teeth in posterior. Creating curves combining these points (see FIG. 19). At the anterior level the curve passes through the middle of the cingulii.

A plane is created passing through these points and curves.

The surface here will be the upper limit of the splint, the part in contact with the teeth of the opposite arch.

Recovery of Profile Lines of the Splint

Cut out the meshing of the mandibular arch, and duplicate it. The cut-out limits correspond to the limits of the splint (see FIGS. 20 to 23).

2 Occlusal Analysis

The orientation of the teeth at the level of the dental arches is done very precisely. The plane passing through the cuspids of the teeth is not flat and is incurved. In the sagittal profile view, it is possible to make out the Spee curve, concave towards the bottom, passing through the canine cusp tip and following the vestibular cuspids of the other teeth. In the frontal view, the Wilson curve, concave towards the top, if applied to the maxillary, joins the apex of the vestibular and lingual cuspids of two homologous teeth (generally the first molars). The Monson sphere 22 (see FIG. 24) is described as: "The Monson sphere, whereof the centre is approximately at the level of the crista-galli apophysis, passes through the mandibular cuspid points and the anterior slope of the mandibular condyle". It could per se give the orientation of the occlusal surface of the teeth and therefore determine the position of the occlusion plane. Different methods have been described to locate the centre of the Monson sphere as only radiographic examination can locate the crista-galli apophysis; the attempt is often made to avoid radiography, if possible.

A first method would consist of determining the radius of curvature of the sphere adapted to the patient by means of a mathematical formula coming from cephalometric analysis. (JD ORTHLIEB).

Another description locates the centre of the sphere at the apex of an equilateral triangle passing through the centre of the condyles.

After study of a range of individuals, the method described by Broadrick is equivalent but does not consider the skeletal type of the patient. In fact, the radius of curvature used is always the same (10.4 cm) and consequently does not systematically suit all patients.

We take inspiration from the technique described by Orthlieb in 1983 and it is this which will be described in our system. But we are not restricted to this method, and evaluation as per according to the clinical case is planned.

The value of the distance between the inter-incisal line and the condyle is shown and used to locate the centre of the sphere on the median sagittal plane. This value is carried over at the level of the canine cusp tip 21 and of the condyle 28, 29 and the centre of the sphere 22 must be situated equidistant from this value relative to these points.

The resulting anatomical cap 23 gives us an idea of the Spee curve in the sagittal view.

For occlusal analysis the interarch contacts are marked in colour, in the static and dynamic position if necessary. Tools exist for retouching the meshing in relation to the teeth by adding or deleting material. The contact points evolve. The cap of the sphere determining the occlusion plane is useful a this time for evaluating poorly positioned teeth and correcting them virtually. When teeth are missing, importing is done from a databank. This charting will be useful for transposing the occlusal adjustment in the mouth. If the majority of adjustments is adjustments by addition, it is proposed to carry out CAD splint, then made of transparent material. It will take up composite material and will then be applied in the mouth to press this composite onto the teeth of the patient in the event where the tooth support must not receive major prosthetic reconstruction as the loss of substance is minimal. In the event where the occlusal rehabilitation project indicates a greater loss of substance, another method consists of making a series of provisional crowns to the shape of our modelling. Once the ideal morphologies are obtained, a reduction is made (for example by adapted software) of future dental abutments, and a mucosal support plate or dental depth control brackets is designed. The piece can be machined in one piece from PMMA. These elements will be reset into the mouth to adapt them to the teeth just after their preparation. It is possible to leave out one or more retouches. Instantaneously the software can recalculate occlusion points and these can be redisplayed. There also follows a modification of the interarch relationship with possible mismatch of the mandibular arch. Its follow-up is ensured to better determine the retouch zones on a given arch. It can be useful to play on the transparency of the meshing for better readability of visible contacts. At all times the recorded movements can be played. During movement the kinematics of the joint can be followed up by displaying the right and left curve in 2D or in 3D. The displacement is transmitted to the arches.

For occlusal therapeutics by orthosis tools are available to apply the method described previously. The splint created is displayed. The specificity of the algorithms developed is that it is possible to exit the plot of the curve. That is, we are not obliged to constrain displacement in some situations to the recorded displacement. This is useful when a pathology is diagnosed and whereof one of its manifestations is a movement incoherent at the articular level. It can be useful to also have multiple useful tools to design all types of splints (mandibular advance for treatment of ronchopathy, hyperdrives in orthodonty, repositioning splint of the maxillary used intraoperatively in maxillofacial surgery . . . ). The approach is almost similar to that described above. The common elements are working on part of the meshing of models placed in a given position.

For orthodontic therapeutics, the challenge is to replace the teeth by means of an appliance so that they are organised coherently on the same arch and relative to the antagonist arch. The occlusion plane is also useful in this case. The tools available are tools for shifting the teeth une via the <<trackball>> type. 3D inspired curves of elements already present (Spee curve, Wilson curve, occlusion plane, and position relative to the articular axis of rotation) are drawn on reference points (cuspid points, incisive edges, vestibular faces). An algorithm ensures alignment between the missing curve and the ideal curve. Once the occlusion points ensuring the interarch wedging and the contacts during dental guides are validated (depending on condyle movement), other tools ensure the design of the orthodonty appliance. Made-to-measure brackets and wires in lingual or vestibular position are produced. Other useful information is knowing the positioning of subjacent roots of the crowns. The volume of these roots is imported, for example originating from an X-ray scanner. An algorithm derived from the algorithm of the marching cube models these roots which are then fused to the crowns of the set up. The digital dental set up is sometimes associated with surgical planning but surgery is done after orthodontic treatment.

3 Orthodonty and Maxillofacial Surgery

The aim of orthodonty is to standardise dento-alveolar ratios to optimise occlusal function. As we have seen previously analysis of occlusal functions is specific and difficult to guide to mouth. Therefore, even in orthodonty, installing models of arches relative to reference planes for studying the kinematics are essential elements. Orthodontic therapeutics often uses orthopaedic appliances whereof the virtual or physical simulator is the support. During treatment and for cases requiring them, surgical repositioning splints of dental arches when the maxillary bone or the mandible have been selected have to be produced.

Prior to treatment, the approach is very similar to what is described for occlusal analysis.

To complete cephalometric radiographic diagnosis, it is possible to simulate dental displacement. The additional function is the <<set up>> function. This function is made highly accessible because it is done digitally and can result to design of the orthodontic appliance. Previously, this was reserved for very precise cases since the technique needed much handling. It can however be democratised, and functions such as 3D plane occlusion make the technique even more reliable. FIG. 28 illustrates a digital set up 24 relative to the occlusal cap 23 derived from the Monson sphere 22.

If a scanner has been used, after reconstruction it is possible to import the volumes of roots 25 and integrate them in the set up by correlation (see FIG. 29). Even if the set up has to be imported within the reconstruction of bone volumes permitted by the scanner, this solution is feasible.

In the event where the scanner is the reference, it is no longer necessary to search reference planes by placement of cutaneous markers. Bone markers are discernible directly.

When diagnosis of dysmorphosis of bone bases is completed, maxillofacial surgery is undertaken. The consequences of this surgery have to be simulated on the models. Maxillary and or mandibular displacements are carried out according to a mandibulo-cranial relation recorded and kept and according to a reference plane (the axio-orbital plane adjacent to the Frankfurt plane). The quantity and direction of displacement of the arches and bone structures supporting them are determined by clinical examination and by cephalometric analysis. The results of this analysis are imported into the software to shift the digital dental arches, just as surgery could do. Splints which can be modelled are made to ensure repositioning of the maxillary bone or bones intraoperatively.

The process according to the invention is very useful for designing appliances such as hyperdrives aimed at stimulating mandibular growth via the mandibular phenomenon of propulsion. This therapeutics needs to know the value of disimpaction of molar sectors, this value depending on the joint and the condyle slope. When the data of the recording of the mandibular kinematics are available, the design of this type of appliance is made easier and reliable.

b. Use of Positioning Data to Ensure Transfer to Commercially Available Virtual Simulators.

We use the axes of symmetry determined by the cutaneous markers and the marking of the condyle points.

As the straight line passes through the condyle point, or bicondyle axis 26, is centred on the hinge axis of the articulator, and the models are placed in the anteroposterior direction. The Frankfurt plane 8 passes at the level of the horizontal branch of the articulator, and the models are placed in the vertical direction. The sagittal plane 9 passes through the axis of symmetry of the articulator (see FIG. 30).

The angular data of the shape of the joint obtained from the kinematics study can be exploited on these systems as can be done via axiography. The angle 27 of the condyle slope is to be carried over to the articulator.

The advantage of the present invention in particular is that capturing of movements improves definition of the dental appliance, for example an inter-occlusal device (splint) but it also introduces the possibility of detecting articular pathologies, and processing them prematurely by means of splints constructed in CAM, from digital data harvested directly from the patient.

Also, this three-dimensional modelling guides the orthodontist in his therapeutic choices: the forces necessary to be applied to the crowns to obtain displacement over time can be calculated exactly.

The invention claimed is:

1. A process for the design of a dental appliance for a facial skeleton of a patient comprising a mandibular and a maxillar dental arch, the process comprising the following steps:
   providing a 3D digital model of said mandibular and maxillar dental arches;
   obtaining reference planes of the facial skeleton by pointing characteristic points of the patient's face with a stylus tracked by a motion capture camera;
   attaching markers to the mandibular arch and to the patient's head, wherein the markers are distinct from the stylus;
   correlating the 3D digital models of the mandibular and maxillar dental arches with the reference planes of the facial skeleton by pointing with the tracked stylus, in the patient's mouth, corresponding points of the models of the dental arches;
   registering the 3D digital models of the mandibular and maxillar dental arches with the markers;
   recording displacements of the mandible with respect to the maxilla of the patient by tracking the markers by the motion capture camera;
   moving the model of the mandibular dental arch with respect to the model of the maxillar dental arch by applying said recorded relative displacements of the mandible and the maxilla to the models of the mandibular and maxillar dental arches.

2. The process of claim 1, further comprising implementing a collision detection algorithm for determining and displaying zones of contact between teeth of the mandible and of the maxilla during movement of the mandibular dental arch.

3. The process of claim 1, wherein the reference planes of the facial skeleton are determined by the following steps:
   picking reference points on the patient's face;
   constructing reference planes passing by said reference points.

4. The process of claim 1, further comprising calculation by rigid transformation to tolerate a slight variation in the situation of markers.

5. The process of claim 4, further comprising calculation by rigid transformation configured to compensate the movements of the facial skeleton during recordation of movements of the mandible.

6. The process of claim 1, further comprising a design and placement step by software of a bracket capable of fixing a shape memory wire and guiding orthodontic traction.

7. The process of claim 1, comprising determining a Monson sphere of the facial skeleton by implementing the following steps:
   measuring the distance between the inter-incisal line of the mandible and the centre of a mandibular condyle,
   placing on the median sagittal plane of the facial skeleton the points located at said measured distance from said mandibular condyle,
   placing on the median sagittal plane the points located at said measured distance from the canine cusp tip,
   wherein both placement steps are conducted to obtain a common point in the placed points, this common point being the centre of the Monson sphere.

8. A system for the design of a dental appliance for a facial skeleton of a patient, said system comprising a motion capture camera, markers detectable by the motion capture camera, a computer and a memory into which is recorded an algorithm adapted to implement the following steps:
   importing a 3D digital model of said mandibular and maxillar dental arches;
   computing reference planes of the facial skeleton based on characteristic points of the patient's face pointed by a stylus tracked by the motion capture camera;
   importing a recordation, by the motion capture camera, of the displacements of the mandible with respect to the maxilla of the patient, wherein the markers are attached to the patient's dental arches;
   correlating the 3D digital models of the mandibular and maxillar dental arches with the reference planes of the facial skeleton;
   moving the model of the mandibular dental arch with respect to the model of the maxillar dental arch by applying said recorded relative displacements of the mandible and the maxilla to the models of the mandibular and maxillar dental arches.

9. The process of claim 1, wherein during the motion capture step a headband comprising a nasal support and carrying the markers is held on the patient's forehead.

10. The process of claim 1, wherein the dental appliance comprises at least one of: an inlay, an onlay, a crown, a bridge and a splint.

\* \* \* \* \*